US010639439B2

(12) United States Patent
Larson

(10) Patent No.: US 10,639,439 B2
(45) Date of Patent: May 5, 2020

(54) SMOKELESS THC AND ADMINISTRATION METHOD THEREOF

(71) Applicant: Raymond Louis Larson, Aliso Viejo, CA (US)

(72) Inventor: Raymond Louis Larson, Aliso Viejo, CA (US)

(73) Assignee: MIDWEST PHARMACEUTICALS, LLC, Coeur D'Alene, ID (US)

( * ) Notice: Subject to any disclaimer, the term of this patent is extended or adjusted under 35 U.S.C. 154(b) by 0 days.

(21) Appl. No.: 14/167,853

(22) Filed: Jan. 29, 2014

(65) Prior Publication Data

US 2014/0209109 A1 Jul. 31, 2014

Related U.S. Application Data

(60) Provisional application No. 61/849,573, filed on Jan. 30, 2013.

(51) Int. Cl.
| | | |
|---|---|---|
| *A61M 15/06* | (2006.01) | |
| *A24B 15/167* | (2020.01) | |
| *A24F 40/10* | (2020.01) | |
| *A61K 31/05* | (2006.01) | |
| *A61K 31/352* | (2006.01) | |
| *A61K 9/00* | (2006.01) | |
| *A61M 11/04* | (2006.01) | |

(52) U.S. Cl.
CPC ........... *A61M 15/06* (2013.01); *A24B 15/167* (2016.11); *A24F 40/10* (2020.01); *A61K 9/007* (2013.01); *A61K 9/0078* (2013.01); *A61K 31/05* (2013.01); *A61K 31/352* (2013.01); *A61M 11/042* (2014.02); *A61M 2205/8206* (2013.01)

(58) Field of Classification Search
CPC ...... A24F 47/002; A24F 47/008; A61M 15/06
USPC ............................ 131/273, 329; 128/202.21
See application file for complete search history.

(56) References Cited

U.S. PATENT DOCUMENTS

| | | |
|---|---|---|
| 6,380,175 B1 | 4/2002 | Hussain |
| 6,503,532 B1 | 1/2003 | Murty |
| 7,676,269 B2 | 3/2010 | Yun |
| 8,252,745 B2 | 8/2012 | Yeomans |

(Continued)

FOREIGN PATENT DOCUMENTS

| | | | | |
|---|---|---|---|---|
| CA | 2455129 A1 * | 2/2004 | ........... | A61K 31/352 |
| WO | WO 2012/072762 A1 * | 6/2012 | | |

OTHER PUBLICATIONS

Ream et al., Smoking tobacco along with marijuana increases symptoms of cannabis dependence, 2008, Drug Alcohol Depend., 95(3), p. 199-208.*

(Continued)

*Primary Examiner* — Anthony Calandra

(57) ABSTRACT

A pharmaceutical composition and administration apparatus includes a portable powered vaporizer with a mouthpiece, smokeless vaporizing element, and a removable chamber. The chamber contains a composition comprising tetrahydrocannabinol (THC), cannabidiol (CBD), FCC grade ethanol, flavoring, pharmaceutical grade nicotine, USP grade aqueous glycerine, USP/EP grade propylene glycol, and USP grade vegetable glycerine. In various formulas the THC may be at concentrations of 1-30%, 30-60% and 60-99%, while CBD concentrations may be 0-15% including other cannabinoids derived from extraction.

14 Claims, 2 Drawing Sheets

(56) References Cited

U.S. PATENT DOCUMENTS

| | | | |
|---|---|---|---|
| 8,551,949 | B2 | 10/2013 | Toll |
| 2007/0112327 | A1 | 5/2007 | Yun |
| 2009/0110724 | A1 | 4/2009 | Giordano |
| 2009/0155186 | A1 | 6/2009 | Stock |
| 2010/0018524 | A1 | 1/2010 | Jinks |
| 2010/0199983 | A1 | 8/2010 | Jinks |
| 2010/0267733 | A1 | 10/2010 | Shytle et al. |
| 2011/0015188 | A1 | 1/2011 | Yun |
| 2011/0029030 | A1 | 2/2011 | Yun |
| 2011/0036346 | A1 | 2/2011 | Cohen et al. |
| 2011/0230549 | A1 | 9/2011 | Guy |
| 2011/0256097 | A1 | 10/2011 | Joonkyoo |
| 2012/0145170 | A1* | 6/2012 | O'Connell .................... 131/298 |
| 2013/0220315 | A1* | 8/2013 | Conley ................. A24F 47/008 128/202.21 |
| 2014/0130817 | A1* | 5/2014 | Li .......................... A24F 47/008 131/329 |
| 2014/0166027 | A1 | 6/2014 | Fuisz et al. |
| 2014/0166028 | A1 | 6/2014 | Fuisz et al. |
| 2014/0209109 | A1 | 7/2014 | Larson |
| 2015/0181924 | A1* | 7/2015 | Llamas .................. A24B 15/16 131/275 |
| 2015/0313868 | A1* | 11/2015 | Morgan ............... A61K 31/352 514/221 |

OTHER PUBLICATIONS

Gentlemans Vapes, The Excutive Kit—Hash Oil Vaporizer, 9/286/2012 (downloaded online Jun. 5, 2015 from archive.org http://gentlesmansvapes.com/products/excutive-4-5-6v-hash-oil-vape).*

Mehmedic et al., Potency Trends of THC and Other Cannabinoids in Confiscated Cannabis Preparations from 1993 to 2008, 2010 J Forensic Sci, vol. 55 No. 5, p. 1209-1217.*

Analytical 360, BHO reclaim (stoney), Apr. 20, 2012 (downloaded online Jun. 5, 2015).*

Patients Care Collective, The Promising Future of Hash Oil, Nov. 10, 2011 (downloaded online May 20, 2015 from archive.org 'http://berkeleypatientscare.com/2011/11/03/the-promising-future-of-hash-oil/'.*

MMJColarado, Post by MMJColarado on MMJPatient, Aug. 21, 2011 (downloaded online May 20, 2015).*

Sour Diesel Oil: budgenius.com, downloaded from archive.org on Aug. 26, 2015 [dated Apr. 1, 2013].*

Hash Oil by CWCC:budgenius.com, downloaded from archive.org on Aug. 26, 2015 [dated Jan. 12, 2012].*

Analytical360.com, Test Results [downloaded online from archive.org], Apr. 25, 2012 [downloaded on Apr. 22, 2016].*

Kinddeliveries.org, Gold Pen w/ Pure Gold Cartridge [downloaded online from archive.org], Dec. 11, 2013 [downloaded on Apr. 21, 2016].*

Moirai, Major Compounds in Cannabis and the Impact to Your High [downloaded online from archive.org], Aug. 30, 2012 [downloaded on Apr. 22, 2016].*

FDA, 21 CFR 211: Code of Federal Regulations Title 21, Apr. 1, 2015.*

McPartland et al., Cannabis and Cannabis Extracts: Greater than the Sum of their Parts?, 2001, Haworth Press, p. 103-132.*

Mentor Capital, Inc, Form 10-Q quarterly period ending Mar. 31, 2016, signed and dated May 10, 2016.*

Myers, The 100 Most Important Chemical Compounds:90 THC, 2007, ABC-CLIO.*

Confused about e-cig type hash oil pens, posts dated Aug. 8, 2012-Aug. 16, 2012 [downloaded online Jul. 12, 2017] FC Vaporizer Review Forum.*

Omicron Vaporizer V2.5 Pink Product data sheet, Aug. 29, 2012 [downloaded on Jul. 13, 2017], www.delta9vapes.com [downloaded from archive.org].*

Cannabis education glossary Cannibinoids, Apr. 18, 2016 [downloaded online Jul. 14, 2017], www.thepureelixier.com.*

Defintion of syringe, downloaded online Apr. 5, 2018 from medterms medical dictionary [www.medicinenet.com].*

Omicron Vaporizer for oils, fuckcombustion.conn [downloaded online from archive.org], May 2012 archive.org date [downloaded on Sep. 20, 2018].*

Tetralabs, tetralabs.com [downloaded online from archive.org], Nov. 2012 archive.org date [downloaded on Sep. 19, 2018].*

Nebula Haze, How do THC, CBN, and CBD Relate to Marijuana Potency (downloaded online from archive.org), Aug. 2013 downloaded on Oct. 17, 2019) (Year: 2013).*

Trofin et al., Long-term Storage and Cannabis Oil Stability, Mar. 2012, Revista de Chimie, 63 (No. 3), p. 293-297. (Year: 2012).*

VA.org,CBD Oil—Uses and Future Military Acceptance [downloaded online from va.org] downloaded on Nov. 18, 2019. (Year: 2019).*

INternational Search Report and Written Opinion of Patentability for PCT/US 15/12397.

* cited by examiner

SMOKELESS THC AND ADMINISTRATION METHOD THEREOF

This application claims the benefit of the filing date of provisional application No. 61/849,573, filed on Jan. 30, 2013.

BACKGROUND

Marijuana plant varieties (*Cannabis setiva, Cannabis indica, Cannabis rederalis*, etc.) contain a variety of compounds, the major psychoactive compound being tetrahydrocannabinol (THC). Other compounds include a variety of additional cannabinoids, including cannabidiol (CBD), which is less psychoactive than THC and believed to have a wider scope of medical applications. Numerous publications report analgesic, antiemetic, and anti-glaucomal effects, among others as resulting from CBD. While typically used recreationally, THC has also been shown to be an effective analgesic, antiemetic, and useful in treating nausea and attendant effects of cancer chemotherapy.

Administration of cannabinoids has evolved over time from the inhalation of marijuana combustion byproducts (i.e., smoking) to oral consumption of marijuana when combined with foods, or the oral consumption of cannabinoid compounds (such as THC and other cannabinoids) in extracted pill form. Additionally, transdermal patches, as discussed in U.S. Pat. No. 6,503,532 have been developed and used in the art. These methods of administration are disfavored however.

When inhaling combustion byproducts, users cannot regulate the percentage of individual cannabinoids entering the lungs. Additionally, undesirable irritating, and potentially toxic or carcinogenic are produced and inhaled as well. The use of orally consumed products such as pills allows users to adjust the quantity of a given cannabinoid ingested, but is disfavored due to the delay of cannabinoid effects caused by the digestive system. Additionally, many marijuana users prefer the mimicry of smoking conferred by inhalation for personal and social reasons. While a transdermal patch may be an effective way of time-releasing a known quantity of particular cannabinoids into the blood stream, this method suffers from drawbacks similar to orally ingested pills, including a lack of social interaction.

For these reasons, there is a need for a cannabinoid composition possessing a predetermined quantity of THC and CBD (in addition to other cannabinoids) for users to obtain a desired recreational, medical or combined effect. There is also a need for an administration technique that allows users to control the quantity of cannabinoids administered through an inhalation apparatus that avoids simple combustion.

SUMMARY

Presented is a formulation of cannabinoid and a smokeless administration of use through vaporization in a portable and rechargeable delivery system. The cannabinoids are mixed with several vegetable glycerols including propylene glycol, among other components. Several cannabinoid formulations with varying levels of THC and CBD are contemplated, and preferably will be contained in a cartridge. In this manner, cartridges can be interchangeable with other cartridges depending on a desired effect.

Two embodiments of cartridges are contemplated, a disposable cartridge and a refillable cartridge. In the instance of a refillable cartridge, a syringe may accompany the delivery system for refilling the cartridge. This is due to the high viscosity of high THC/CBD percentage formulations and the attendant difficulty of transferring them from a source vessel into a refillable cartridge.

DESCRIPTION

Figure 1:
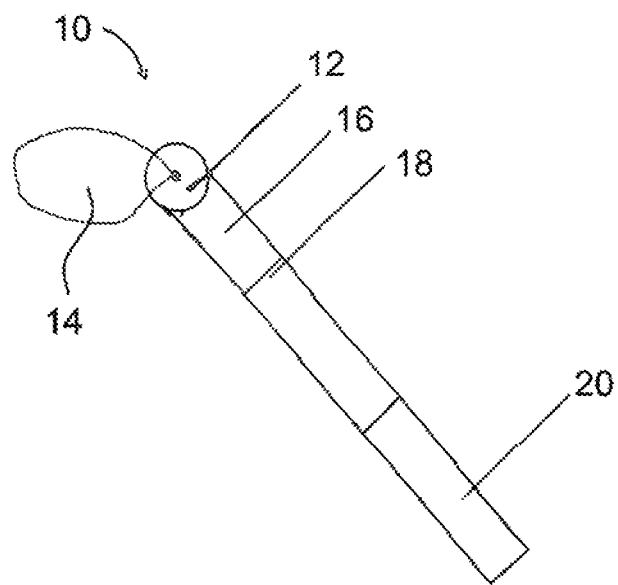
FIG. 1 shows a disposable smokeless "e-cigarette" type vaporizing apparatus.

An improved pharmaceutical composition and administration apparatus is disclosed. The administration apparatus comprising a portable powered vaporizing apparatus having a mouthpiece, a smokeless vaporizing element, and a removable chamber. Portable vaporizers of this variety are typically known as e-cigarettes, which have a heating element for vaporizing nicotine and nicotine-containing oils. In the embodiments disclosed herein, a heating element calibrated for the use cannabinoids is contemplated.

When prepared for use, the chamber contains a cannabinoid composition comprising tetrahydrocannabinol (THC), cannabidiol (CBD), FCC grade ethanol, flavoring, pharmaceutical grade nicotine, USP grade aqueous glycerine, USP/EP grade propylene glycol, and USP grade vegetable glycerine.

Preferably a food grade ethanol and flavoring is used in the composition. Additionally, in one preferred embodiment, the nicotine may include USP grade nicotine extract, and may be extracted from organic sources.

In one preferred embodiment the food grade glycerin will comprise a 99.7% USP Grade Glycerine having 99.70% Glycerol content, 0.3% maximum moisture content, 10 ppm max chlorides, 10 max (APHA) coloring, a minimum specific gravity of 1.2612, 20 ppm max, 5 ppm max heavy metals, 30 ppm max chlorinated compounds, 100 ppm max residue on ignition, 1.000% max fatty acid and esters, 0.5% water, and assayed at between 99.0 to 101.0% (on a dry basis). Additionally the food grade glycerine passes tests for DEG and related compounds and organic volatile impurities. In another embodiment pure vegetable glycerin may be used.

Preferably the propylene glycol selected for usage will be pharmaceutical grade propylene glycol with a specified purity greater than 99.8%, and in compliance with United States Pharmacopeia (USP), European Pharmacopeia (EP), Japanese Pharmacopeia (JP) and Food Chemical Codex (FCC) standards.

Several formulas are contemplated when formulating the pharmaceutical composition. In all cases, where 0% is listed, it is understood that any amount under the maximum percentage down to greater than 0% is intended, including trace amounts. A first formula includes a 30% THC:

| | |
|---|---|
| 0% to 30% | Tetrahydrocannabinol (THC) |
| 0% to 15% | Remaining cannabinoids including cannabidiol (CBD) |
| 0% to 20% | FCC grade ethanol |
| 0% to 04% | Food grade flavoring |
| 0% to 03% | Pharmaceutical grade nicotine |

-continued

| | |
|---|---|
| 0% to 20% | USP grade acqueous glycerine |
| 0% to 70% | USP/EP grade propylene glycol |
| 0% to 25% | USP grade vegetable glycerine |

A second formula combines known cannabinoids THC and CBD at specific concentrations:

| | |
|---|---|
| 0% to 30% | Tetrahydrocannabinol (THC) |
| 0% to 15% | Cannabidiol (CBD) |
| 0% to 15% | Remaining cannabinoids excluding cannabidiol (CBD) |
| 0% to 20% | FCC grade ethanol |
| 0% to 04% | Food grade flavoring |
| 0% to 03% | Pharmaceutical grade nicotine |
| 0% to 20% | USP grade acqueous glycerine |
| 0% to 70% | USP/EP grade propylene glycol |
| 0% to 25% | USP grade vegetable glycerine |

A third formula combines employs a greater percentage of THC along with other known cannabinoids including cannabidiol at a lower percentage, and reduced percentages of aqueous glycerine and propylene glycol:

| | |
|---|---|
| 30% to 60% | Tetrahydrocannabinol (THC) |
| 0% to 15% | Remaining cannabinoids including cannabidiol (CBD) |
| 0% to 20% | FCC grade ethanol |
| 0% to 04% | Food grade flavoring |
| 0% to 03% | Pharmaceutical grade nicotine |
| 0% to 10% | USP grade acqueous glycerine |
| 0% to 60% | USP/EP grade propylene glycol |
| 0% to 25% | USP grade vegetable glycerine |

A fourth formula comprises the higher percentage of THC but with a known quantity of CBD in addition to remaining cannabinoids. As with the previous formula, the aqueous glycerine and propylene glycol are reduced, but in this case including the USP vegetable grade glycerine as well.

| | |
|---|---|
| 30% to 60% | Tetrahydrocannabinol (THC) |
| 15% to 30% | Cannabidiol (CBD) |
| 0% to 15% | Remaining cannabinoids excluding cannabidiol (CBD) |
| 0% to 20% | FCC grade ethanol |
| 0% to 04% | Food grade flavoring |
| 0% to 03% | Pharmaceutical grade nicotine |
| 0% to 10% | USP grade acqueous glycerine |
| 0% to 60% | USP/EP grade propylene glycol |
| 0% to 15% | USP grade vegetable glycerine |

A fifth formula comprises the maximum percentage of THC. With this formula, it is intended that either replaceable cartridges or a syringe will be used due to the higher viscosity of the pharmaceutical composition. Additionally, in this formulation, a much reduced quantity of aqueous glycerine, propylene glycol and vegetable glycerine is used:

| | |
|---|---|
| 60% to 99% | Tetrahydrocannabinol (THC) |
| 0% to 10% | Remaining cannabinoids including cannabidiol (CBD) |
| 0% to 20% | FCC grade ethanol |
| 0% to 04% | Food grade flavoring |
| 0% to 03% | Pharmaceutical grade nicotine |
| 0% to 10% | USP grade acqueous glycerine |
| 0% to 40% | USP/EP grade propylene glycol |
| 0% to 10% | USP grade vegetable glycerine |

The sixth formula adds a known quantity of CBD to the high concentration of THC in the formula. Due to the high percentage of THC and CBD, the remaining cannabinoids are reduced as well as the aqueous glycerine, propylene glycol and vegetable glycerine:

| | |
|---|---|
| 60% to 99% | Tetrahydrocannabinol (THC) |
| 0% to 15% | Cannabidiol (CBD) |
| 0% to 10% | Remaining cannabinoids excluding cannabidiol (CBD) |
| 0% to 20% | FCC grade ethanol |
| 0% to 04% | Food grade flavoring |
| 0% to 03% | Pharmaceutical grade nicotine |
| 0% to 10% | USP grade acqueous glycerine |
| 0% to 40% | USP/EP grade propylene glycol |
| 0% to 10% | USP grade vegetable glycerine |

In all embodiments it is preferable to have an administration apparatus that is a vaporizer having a mouth piece, a chamber for holding a quantity of the pharmaceutical composition, and a battery powered heating element. A preferable administration apparatus may include an "e-cigarette" type apparatus in which a battery powered heating element is combined with a chamber for holding a preferred cannabinoid formulation. The cannabinoid formulation is drawn from the chamber and heated by the heating element to a vaporization temperature at which point the vapors are inhaled in by a user.

Referring to FIG. 1, one common type of preferred and inexpensive administration apparatus is a onetime use only disposable e-cigarette vaporizer 10. The disposable e-cigarette vaporizer 10 includes a mouthpiece 12 for extracting vaporized cannabinoids 14, the mouthpiece 12 is in fluid communication with an atomizer 16 which combines vaporized cannabinoids 14 with air drawn through the disposable e-cigarette vaporizer 10. The atomizer 16 is powered by a battery 18 adapted to power the atomizer 16 sufficiently to vaporize a quantity of cannabinoids housed in a chamber 20 in fluid communication with the atomizer 16. In this embodiment, once the chamber 20 is empty or the battery 18 dies, the entire apparatus is discarded.

Figure 2:
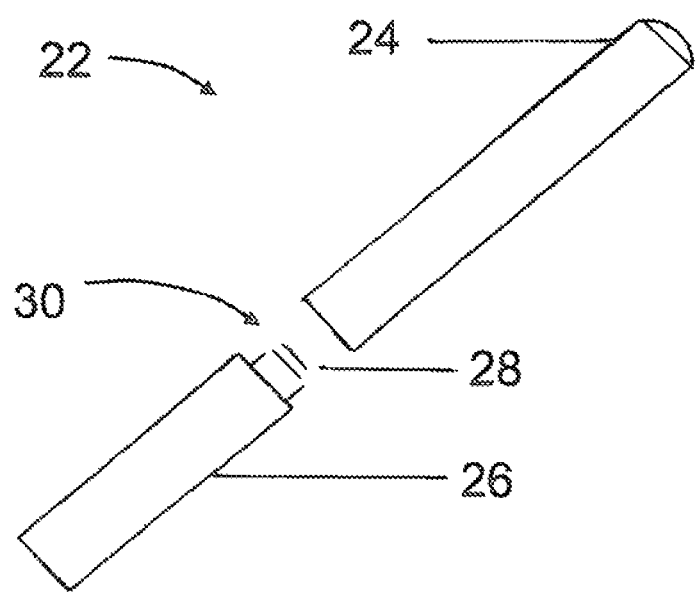
FIG. 2 shows a smokeless "e-cigarette" type vaporizing apparatus having a disposable cartridge.

Referring to FIG. 2, a second type of preferred administration apparatus includes a replaceable cartridge vaporizer 22. The replaceable cartridge vaporizer 22 includes a battery 24. A chamber 26 and atomizer 28 are connectable to the battery 24 using a threaded connection 30. In this manner, the chamber 26 may be replaceable once a quantity of cannabinoid formula housed in the chamber 26 is exhausted. This apparatus may be preferable since the battery 24 is capable of vaporizing a quantity of cannabinoid formula in multiple chambers.

Figure 3:
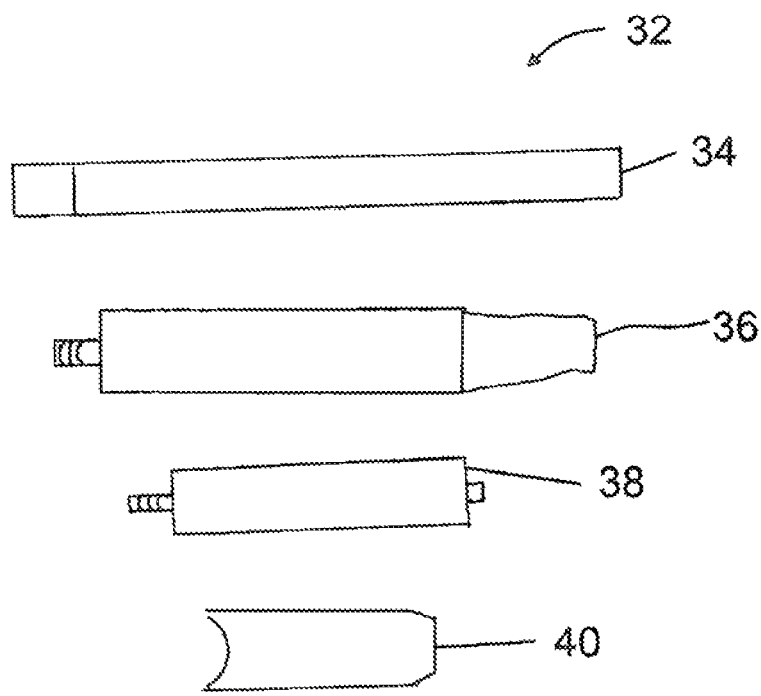
FIG. 3 shows a disassembled smokeless "e-cigarette" type vaporizing apparatus having a refillable cartridge.

Referring to FIG. 3, a third type of preferred administration apparatus is a commonly used e-cigarette vaporizer 32. In this embodiment the components of the e-cigarette vaporizer 32 may be disassembled into a battery 34, either a disposable cartridge 36 or refillable cartridge 38, and a mouthpiece 40. The battery 34 is preferably combined with an atomizer (not shown). Also, in instances where a disposable cartridge 36 is used, the disposable cartridge 36 may have a mouthpiece incorporated therein.

Figure 4:
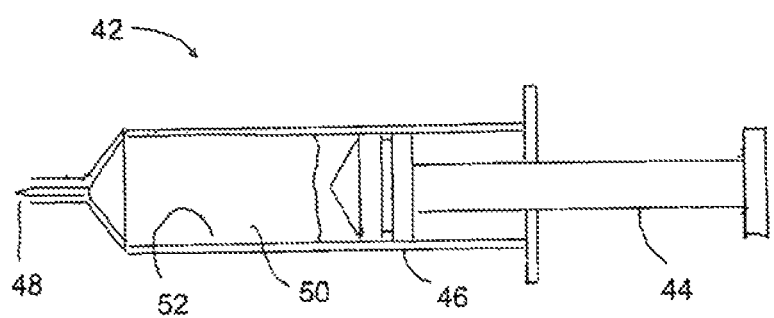
FIG. 4 shows a syringe used to refill the cartridge of a refillable "e-cigarette" type vaporizing apparatus.

Referring to FIG. 4, in certain instances, where a refillable cartridge 36 is used, the cannabinoid formulation may be too viscous for easy decanting into a refillable cartridge 36. In such an instance, a syringe 42 may be employed. It is anticipated that a typical syringe having a plunger 44, barrel 46 and needle 48 will be used, although the needle may be adapted and sized for an efficient union with the refillable cartridge 36 (FIG. 3). While the syringe 42 may be used to take up a cannabinoid mixture 50 into the barrel interior 52, it is also anticipated that syringes may be produced and purchased pre-loaded with a cannabinoid mixture 50, ready for introduction into an empty cartridge 36. In this manner cartridges may be easily and effectively refilled with a desired cannabinoid formulation.

When properly administered, the pharmaceutical composition of the present invention may be useful for both recreational and medical purposes. Medical uses may include, but are not limited to, treating pain, nausea, loss of appetite (particularly nausea associated with chemotherapy in cancer treatments), glaucoma, arthritis, dementia, multiple sclerosis, and for deterring weight loss.

While the apparatus and associated formulas have been described in detail with reference to specific embodiments thereof, it will be apparent to one skilled in the art that various changes and modifications can be made therein without departing from the spirit and scope thereof. Thus, it is intended that the present description cover the modifications and variations of the invention provided they come within the scope of the appended claims and their equivalents.

What is claimed is:

1. A portable system comprising:
   a) a vaporizer comprising:
      i) a refillable or disposable cartridge, in communication with an atomizer, the cartridge filled with a liquid composition comprising 30% wt.-60% wt. tetrahydrocannabinol (THC), 15% wt.-20% wt. cannabidiol (CBD), 10% wt.-15% wt. cannabinoids other than THC and CBD, and trace-3% wt. nicotine, wherein the cartridge includes an interior chamber;
      ii) a battery connection in electrical communication with the atomizer; and
      iii) a mouthpiece in fluid communication with the atomizer.

2. The portable system of claim 1, wherein the liquid composition comprises 11% wt.-15% wt. cannabinoids other than THC and CBD.

3. The portable system of claim 2, wherein the liquid composition comprises 12% wt.-15% wt. cannabinoids other than THC and CBD.

4. A portable system comprising:
   a) a vaporizer comprising:
      i) a refillable or disposable cartridge, in communication with an atomizer, the cartridge filled with a liquid composition comprising 60% wt.-95% wt. tetrahydrocannabinol (THC), 5% wt.-15% wt. cannabidiol (CBD), greater than 0% wt.-10% wt. cannabinoids other than THC and CBD, and trace-3% wt. nicotine, wherein the cartridge includes an interior chamber;
      ii) a battery connection in electrical communication with the atomizer; and
      iii) a mouthpiece in fluid communication with the atomizer.

5. The portable system of claim 4, wherein the liquid composition comprises 2% wt.-10% wt. cannabinoids other than THC and CBD.

6. The portable system of claim 5, wherein the liquid composition comprises 6% wt.-10% wt. cannabinoids other than THC and CBD.

7. A portable system comprising:
   a) a vaporizer comprising:
      i) a refillable or disposable cartridge, in communication with an atomizer, the cartridge filled with a liquid composition comprising 30% wt.-46% wt. tetrahydrocannabinol (THC), 15% wt.-20% wt. cannabidiol (CBD), greater than 0% wt.-15% wt. cannabinoids other than THC and CBD, and trace-3% wt. nicotine, wherein the cartridge includes an interior chamber;
      ii) a battery connection in electrical communication with the atomizer; and
      iii) a mouthpiece in fluid communication with the atomizer.

8. The portable system of claim 7, wherein the liquid composition comprises 2% wt.-15% wt. cannabinoids other than THC and CBD.

9. The portable system of claim 8, wherein the liquid composition comprises 3% wt.-15% wt. cannabinoids other than THC and CBD.

10. A portable system comprising:
    a) a vaporizer comprising:
       i) a refillable or disposable cartridge, in communication with an atomizer, the cartridge filled with a liquid composition comprising 60% wt.-81% wt. tetrahydrocannabinol (THC), 3% wt.-15% wt. cannabidiol (CBD), 5% wt.-10% wt. cannabinoids other than THC and CBD, and trace-3% wt. nicotine, wherein the cartridge includes an interior chamber;
       ii) a battery connection in electrical communication with the atomizer; and
       iii) a mouthpiece in fluid communication with the atomizer.

11. The portable system of claim 10, wherein the liquid composition comprises 6% wt. 10% wt. cannabinoids other than THC and CBD.

12. The portable system of claim 11, wherein the liquid composition comprises 7% wt. 10% wt. cannabinoids other than THC and CBD.

13. A portable system comprising:
    a) a vaporizer comprising:
       i) a refillable or disposable cartridge, in communication with an atomizer, the cartridge filled with a liquid composition comprising 90% wt.-92% wt. tetrahydrocannabinol (THC), 3% wt.-5% wt. cannabidiol (CBD), 5% wt.-7% wt. cannabinoids other than THC and CBD, and trace-3% wt. nicotine, wherein the cartridge includes an interior chamber;
       ii) a battery connection in electrical communication with the atomizer; and
       iii) a mouthpiece in fluid communication with the atomizer.

14. The portable system of claim 13, wherein the liquid composition comprises 6% wt.-7% wt. cannabinoids other than THC and CBD.

* * * * *